United States Patent [19]

Andera et al.

[11] Patent Number: 4,844,607
[45] Date of Patent: Jul. 4, 1989

[54] VISION TESTER WITH COLOR CORRECTED ILLUMINATING SYSTEM

[75] Inventors: Joseph F. Andera, Palatine; Pete Kaldis, Chicago, both of Ill.

[73] Assignee: Stereo Optical Company, Inc., Chicago, Ill.

[21] Appl. No.: 183,398

[22] Filed: Apr. 13, 1988

Related U.S. Application Data

[63] Continuation of Ser. No. 792,486, Oct. 29, 1985, abandoned.

[51] Int. Cl.$^4$ ............................................. A61B 3/02
[52] U.S. Cl. ................................... 351/243; 351/213; 351/233
[58] Field of Search ............... 351/233, 234, 235, 236

[56] References Cited

U.S. PATENT DOCUMENTS

| | | | |
|---|---|---|---|
| 4,043,646 | 8/1977 | Heine | 351/213 |
| 4,155,632 | 5/1979 | Wolbarsht | 351/243 |
| 4,180,323 | 12/1979 | Persson | 351/208 X |
| 4,452,515 | 6/1984 | Lewis | 351/243 |

Primary Examiner—Rodney B. Bovernick
Attorney, Agent, or Firm—Lockwood, Alex, FitzGibbon & Cummings

[57] ABSTRACT

A color-corrected vision testing apparatus and method are provided, such having a blue filtered incandescent illuminating source in a light-occluding housing for high contrast translumination of test patterns also in said housing to obtain improved testing of acuity levels.

16 Claims, 2 Drawing Sheets

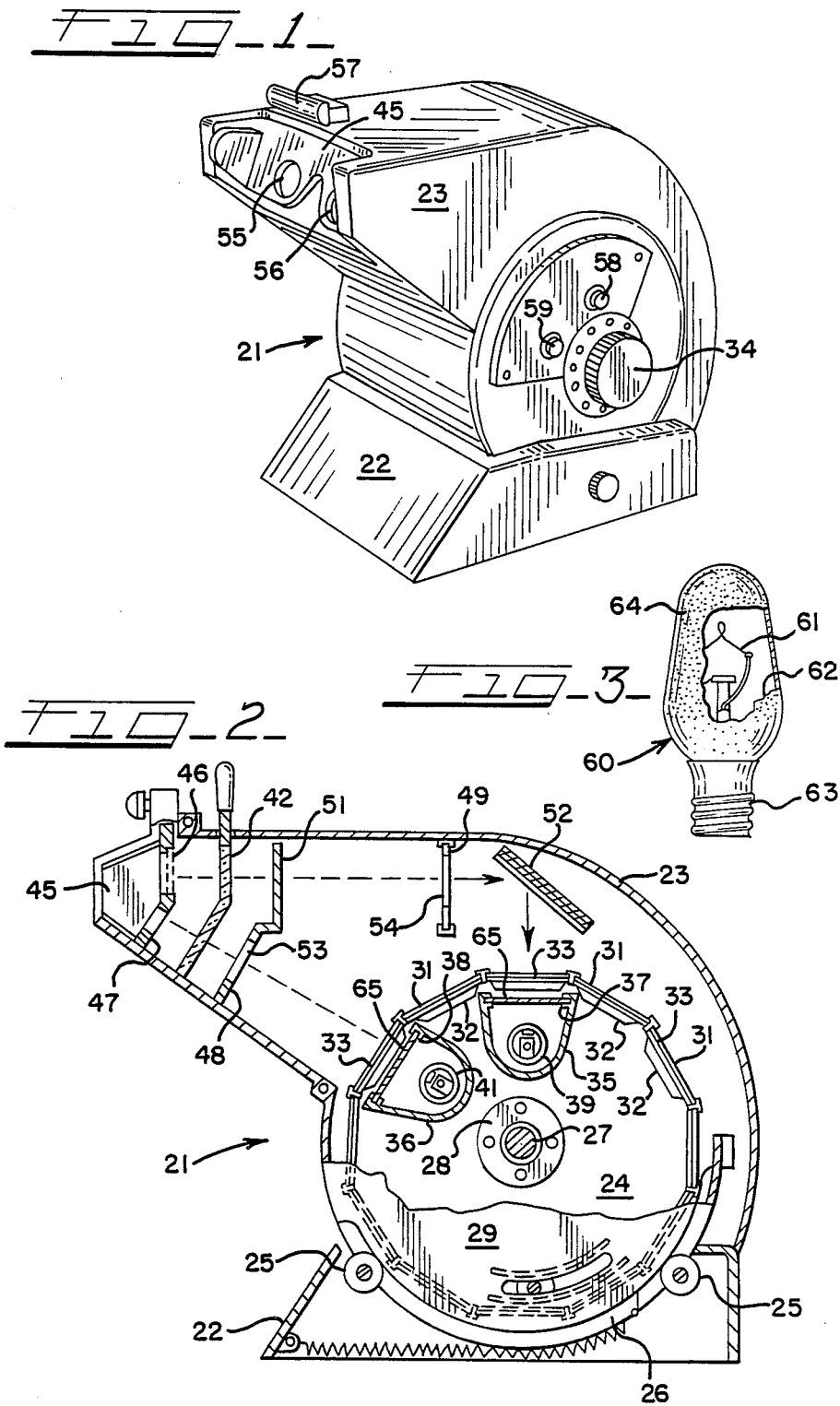

VISION TESTER WITH COLOR CORRECTED ILLUMINATING SYSTEM

This application is a continuation of application Ser. No. 792,486, filed Oct. 29, 1985, now abandoned.

BACKGROUND AND DESCRIPTION OF THE INVENTION

The present invention relates generally to vision testing apparatus, as well as a method of testing vision, which makes use of a light-occluding housing having vision testing transparencies movable into a viewing position relative to a viewing area and having a light source to illuminate the transparencies for viewing. In an important aspect of the invention, the illumination source is color-corrected in order to achieve translumination of an especially white character to provide maximum contrast, high resolution and true color rendition for accomplishing visual evaluations that are of enhanced accuracy and reproducibility.

Vision testers that incorporate light-occluding housings and illuminated transparencies have been available for many years and are used for a number of purposes particularly in the area of testing individuals in connection with obtaining driving licenses. Including this extensive use as well as other uses, such apparatus tests far point acuity, depth perception, color perception, lateral-vertical phoria, near point acuity and lateral near point phoria. The relatively simple construction of these testers as well as their versatility establish a substantial demand for them by governmental agencies, schools, opthamologists and optometrists.

The human eye is a living optical system and its characteristics vary widely from individual to individual and, for a given individual, may vary from day to day and even hour to hour. The ability to recognize small, fine details is visual acuity. Normal acuity is defined as 1.0, or more commonly expressed as 20—20 vision. The basic problem is to establish "normal" conditions in the testing of eyesight. The basic standard which has been sought after is commonly referred to as high noon sunlight under ideal conditions, but to test only under such actual sunlight conditions is impractical, if not impossible since artificial illumination must be used. Visual acuity is a function of object brightness. At low illuminations the eye is colorblind. Maximum contrast enhances acuity. Reducing the contrast of the target will also reduce acuity.

As a part of this invention it has been found that the most effective testing of acuity and other properties of the eye is obtained when the light source casts an illumination that synthesizes the noon daylight condition. The governing factor is the amount of energy which reaches and triggers the retina cell into responding. The eye is a poor photometer inasmuch as it is very inaccurate at judging the absolute level of brightness, but it is excellent in comparing brightness or color of two adjacent areas. Thus, variation in brightness contrast is an excellent basis for vision testing but this has not been adequately achieved by equipment now available.

The light sources or bulbs used in current vision testing equipment of the type under consideration have commonly been coated white. It has been found that the illumination provided thereby in this type of equipment, however, is not true white; for example, at approximately 108 volts the light emitted or transluminated has an orange tinge while at 132 volts the light becomes more yellow. Average voltage supplied to homes and commercial establishments is approximately 117 to 120 and the supply will vary, sometimes considerably depending upon demand, and it is not infrequent that surges result. Thus, the quality of the light or illumination used in the type of testing apparatus under consideration can constitute the weakest and most changeable function of such apparatus and, therefore, can create a serious problem as far as effective use of such apparatus is concerned.

In summary, the present invention deals with an improvement in vision testing and apparatus therefor, such apparatus including a light-occluding housing having vision testing transparencies movable into a viewing position relative to a viewing area, and light source means positioned relative to said transparencies to illuminate same for viewing. The improvement involves the provision of colored filtering means interposed between the light source and the viewing area, with the filtering and light source means cooperatively providing illumination that substantially simulates daylight conditions. In an important aspect of the invention, the filtering means is blue colored and the illumination is in the range of approximately 5000 to 5500 degrees K. The subject invention deals with a vision tester having a color-corrected illuminating system which will simulate ideal daylight lighting conditions as accurately as possible and will minimize detectable variations therein over the range of voltage variations that are typically encountered by this type of apparatus and method.

It is accordingly a general object of the present invention to provide an improved vision testing device and method.

Another object of this invention is to provide an improved eye testing device and method with color-correcting characteristics.

Another object of the present invention is to provide an improved eye testing device and method that provide translumination which achieves maximum contrast, high resolution and true color rendition without increasing heat generation.

Another object of the present invention is an improved eye testing device and method that is capable of providing a reproducible illumination standard which is substantially consistently maintained in the face of variations in input line voltage.

Another object of this invention is to provide an improved eye testing device and method that achieves translumination in the range of daylight conditions of between about 5000 and about 5500 degrees K.

Another object of the present invention is to provide an improved method and apparatus for accurately testing night vision, contrast sensitivity, and color perception, and the onset of cataracts.

BRIEF DESCRIPTION OF THE DRAWINGS

The features of the present invention which are believed to be novel are set forth with particularity in the appended claims. The invention, together with further objects and advantages thereof, may best be understood with reference to the following description taken in conjunction with the accompanying drawings, in the several figures of which like reference numerals identify like elements, and in which:

FIG. 1 is a perspective view of a known form of vision tester;

FIG. 2 is a partial vertical sectional view of the vision tester of FIG. 1;

FIG. 3 is a partly fragmented view of the type of light source preferred to be used in the present invention.

DESCRIPTION OF THE PARTICULAR EMBODIMENTS

Figure 4:
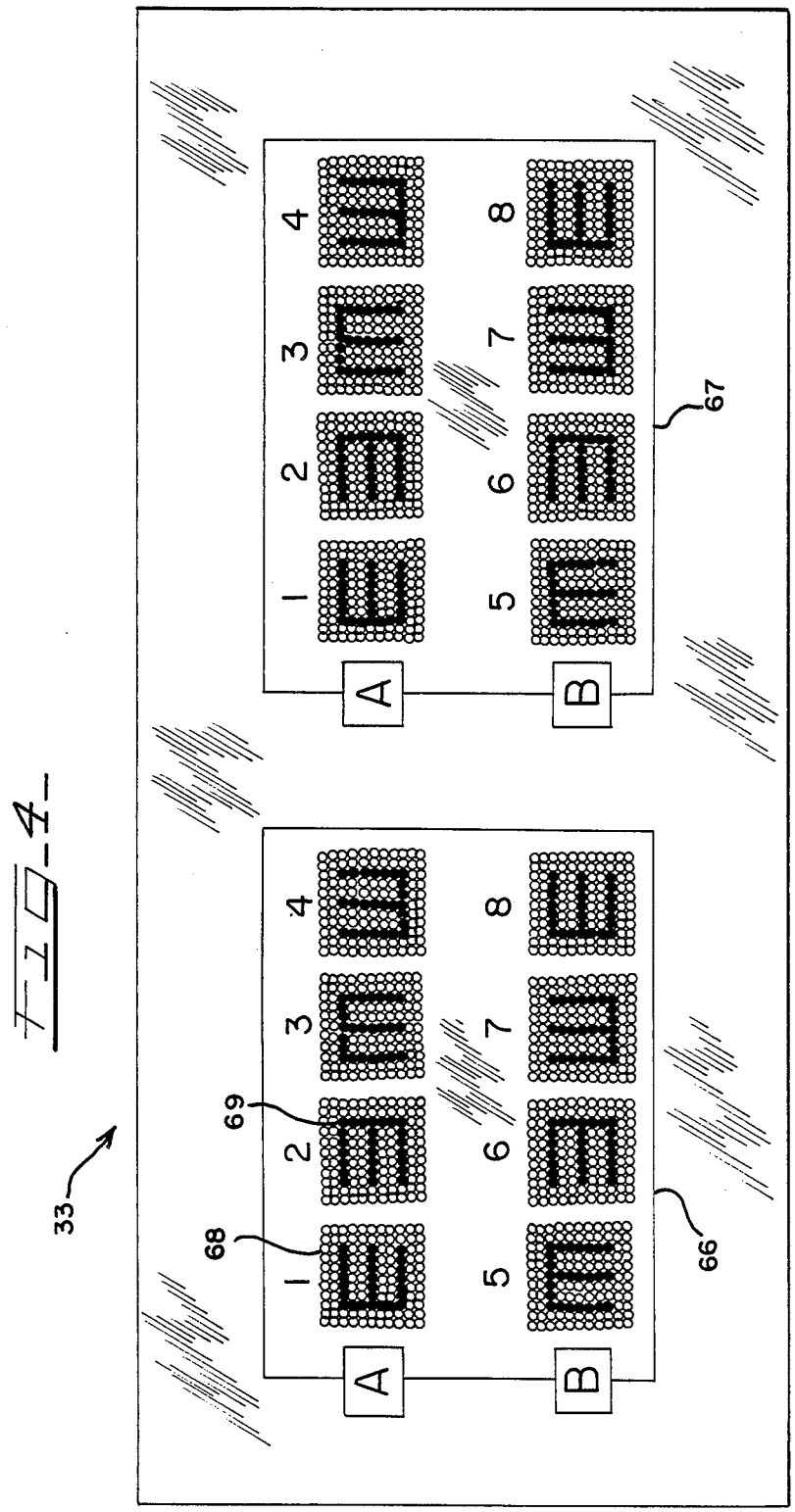
FIG. 4 is a plan view of a typical standard form of stereo transparency for color blindness vision testing.

The vision testing apparatus of FIGS. 1 and 2 is of a known type and is fully described in U.S. Pat. No. 4,452,515. The disclosure of said patent is incorporated herein by reference. The basic vision testing apparatus, generally designated as 21, includes a base member 22, a casing or housing 23, and a rotatable drum member 24 (FIG. 2) which is supported on the base member 22 by rotation means such as guide rollers 25 within a guideway 26. The drum member 24 is mounted to the casing 23 by means of a shaft 27 mounted to hubs 28 in the sidewalls 29 of the casing 23.

Rotatable drum member 24 includes a plurality of rectangular apertures 31 which are circumferentially disposed thereon, each aperture 31 being associated with a holder means 32 for positioning and securing test pattern or transparency 33 at each aperture 31. Each test pattern 33 typically includes a pair of slide transparencies that are positioned and mounted so as to effect a stereo image that is well suited for checking vision quality and capability. Such a transparency 33 is illustrated in FIG. 4, this particular form of transparency being designed to test for color perception. A position indicating dial 34 is mounted onto the shaft 27, and the operator rotates the drum member 24 by turning the dial 34 in order to position a particular test pattern 33 at a desired location within the casing 23 along the circumference of the drum member 24.

A far point test station 35 and a near point test station 36 are mounted within the casing 23 interior of the disk member 24, each such test station 35, 36 having a window 37, 38 and an illuminating means or light source 39, 41 respectively. If desired, each test station 35 or 36 may have dual windows, illuminating means, and compartments housing same in order to enhance the stereo effect. By moving the position indicating dial 34, the operator can align a selected test pattern 33 with either the far point test station 35 or the near point test station 36, and this location is secured by suitable means. Alternatively, an additional set of lenses may be selectively interposed within the sight path in order to adjust the viewing test distance as desired. Filtering assembly 42 may be interposed along the sight path in order to reduce the contrast at the test pattern 33.

A viewing assembly 45 is positioned at a location of the casing remote from the test stations 35 and 36, the viewing means including a far point lens system 46 and a near point lens system 47. Positioned between the near point lens system 47 and the near point test station 36 is a near point divider member 48 for assisting in maintaining the integrity of the line of sight between the near point lens system 47 and the near point test station 36. Positioned between the far point lens system 46 and the far point test station 35 is a far point divider member 49. A septum 51 to facilitate fusion of the slides for a stereo optical effect is positioned between the far point divider member 49 and the far point lens system 46. An optical means 52 is located along the line of sight between the far point divider member 49 and the far point test station 35. Typically, the optical means 52 is in the form of a highly reflective surface, such as a mirror that is visually aligned with the far point lens system 46 so that the plane of the test pattern or target slide transparency 33 that is aligned with the far point test station 35 will be substantially normal to the line of sight.

With more particular reference to the near point divider member 48 and the far point divider member 49, each has a pair of openings 53, 54. The openings 53 are in alignment with the near point lens system 47 and serve as separate apertures for defining the field of vision for the near point stereo testing. The pair of openings 54 are in alignment with the far point lens system 46 and serve as separate apertures for defining the far field of stereo vision. The septum 51 assists in optically merging the stereo test object components or characters located at the far test station 35.

The person being tested looks through viewing openings 55, 56 of the viewing assembly 45, typically while resting his or her head against a forehead rest 57. When the operator of the device 21 wishes to have the person being tested view the pair of stereo slide transparencies or test pattern 33 at the near point test station 36, the operator turns on the near point illuminating means 41 by the operation of suitable circuitry (not shown) while the far point illuminating means 39 remains unlit, with the result that the viewer's line of vision will be automatically directed to the near point test station 36. Likewise, when the operator wishes to have the person being tested view the pair of stereo slide transparencies or test pattern 33 at the far point test station 35, the far point illuminating means 39 is lit, while the near point illuminating means is unlit.

As a means for assisting the operator, the rotatable drum member 24 can include a pair of openings within which are typically mounted a far point indicator lens 58 and a near point indicator lens 59. When the device 21 is in its far point viewing mode, light from the far point illuminating means 39 will be visible through the far point indicator lens 58, while the near point indicator lens 59 will remain dark. Putting the device 21 in its near point vision testing mode will permit the operator to observe light from the near point illuminating means 41 through the near point indicator lens 59, while the far point indicator lens 58 remains darkened. A suitable opening (not shown) is provided in the housing or casing 23 to permit transparencies or slides to be removed and replaced on the drum for varying testing purposes.

The standard type of vision testing apparatus just described has many advantages, such as being compact, readily portable and easy to operate. The present invention deals with substantially improving the efficiency and effectivenes of its use while retaining all of the foregoing desirable characteristics. As referred to herein above, it has been common to utilize incandescent bulbs as the source of light in this type of vision testing apparatus. Such bulbs typically are clear and uncoated or have been provided with a white coating on the external or internal surface thereof which not only does not enhance the brightness or contrast characteristics of the system but also transmits an off-color condition. For example, an orange tinge of color can be noticed at approximately 108 volts, which color changes as the voltage changes and at, for example, 132 volts this off-color becomes more yellow. Unusual voltage drops, to as low as 100 volts and below, increase the orangeness of the illumination over that observed at about 108 volts. For the purpose of this invention, color will be described by a temperature (degrees K) which is a standard comparison of the color of a light source with the color of a black body heated to varying temperatures. Using this standard of measurement, the conventional incandescent bulb even with a tungsten filament and a white coating provides a brightness of only about 2350 degrees K. Conversely, high noon daylight under ideal conditions provides a truer white illumination measured at approximately 5500 degrees K.

Because of the much lower illumination color temperature provided by an incandescent bulb, maximum contrast (black on white) in the illumination or projection of the testing transparencies is not obtained. Additionally, an incandescent bulb will exhibit a loss in efficiency following continued use and any variation in line voltage will also materially adversely affect illumination consistency. As stated earlier, the normally used incandescent bulb will add color, which addition detracts from the effectiveness of a color perception test. Even less desirable is the fact that observation tests show that the human eye detects difference in this added color as the voltage to the bulb varies during voltage surges and drops. Most significantly, when the present invention is practiced, the human eye does not detect color change (although a change in intensity or lumens can be detected) during a voltage surge and drop range of between 135 volts and 110 volts or 100 volts and lower. The high constrast black or white illumination that is characteristic of the present invention persists during such voltage variations.

FIG. 3 illustrates an improved incandescent light bulb 60 designed for use in the vision testing apparatus of the subject invention. This bulb is of conventional configuration and, of course, can be of any suitable configuration to be received within the apparatus. The bulb has a tungsten filament 61 enclosed in the usual clear glass bulb portion 62 provided with a base 63 of the screw type or any other suitable type. Applied to the surface of the glass bulb portion 62 is a blue filtering coating 64 which filters the light emitted by the bulb 60. The coating 64 may be hydrostatically deposited on the glass portion of the bulb. Other means may be used, for example by using dipping or electrostatic techniques or the like.

The thickness and/or density of the coating (whether on a bulb or a separate filter) may vary as long as the coating is capable of filtering (color correcting) the light emitted by the bulb to an extent to increase the contrast thereof so as to obtain a color temperature of approximately 5000 to 5500 degrees K, preferably on the order of about 5000 to 5200 degrees K. Providing this illumination temperature involves taking a number of variables into consideration, including the shade of blue color, the thickness of the coating, the density of the coating, the wattage of the light source, and the closenss of the colored substrate to the light source.

For example, if the coating is too thick or too dense, the resulting illuminating light that is emitted would have too high of a color temperature and would be tinged with blue, which would not be desirable. If the coating is too thin or not sufficiently dense, the resulting illuminating light would be tinged with yellow, and the color temperature would be too low. Also, a 7 watt tungsten filament bulb may be used. If a 10 watt tungsten filament bulb is used, a thicker or more dense coating will be required to obtain the desired color temperature, all other variables being equal. Generally speaking, the farther the colored substrate is from the light source, the thinner or less dense must be the coating.

While FIG. 3 shows the preferred embodiment of the invention, namely, use of a coated bulb, a suitable filter can be placed anywhere in the system as long as it is capable of enhancing color-corrected emission to obtain the requisite maximum contrast. Referring to FIG. 2, plate-like diffusers 65 at each of the test stations 35 and 36 may be blue tinted in order to provide a color-correcting element between the light sources 39 and 41 and the slide transparencies 33. The diffusers 65 can be made from transparent plastic or plate glass with the blue coating applied as indicated above.

As referred to above, FIG. 4 illustrates a typical color blindness slide transparency 33. For the stereo effect, the transparency has duplicate sections 66 and 67 with each test pattern including lines "A" and "B". In each line there is a test pattern suitably numbered for ready identification by the operator, each test pattern including small background circles of color 68 and a letter of differing color 69. The colors are suitably selected to test the ability of the user to identify each letter of each block surrounded by low contrasting color. As this type of test is designed to establish a high degree of difficulty in color discernment for the person being tested, the effectiveness of the test can be materially reduced if the degree of contrast desired is not duplicated by the testing apparatus or if the apparatus imparts colored illumination to the differing colors of the slide. Under such demanding conditions, it is important for the testing apparatus to provide maximum contrast, high resolution and true color rendition. The use of light according to the invention permits these goals to be attained thus resulting in more accurate visual evaluations. Acuity level at maximum contrast (defined in terms of black on white) is attained.

The present invention provides additional advantages. One of the many advantages of the particular form of vision testing apparatus disclosed herein is that the test pattern is enclosed in a light-occluding housing which eliminates exterior light bias. While this advantage is well recognized, it must be also recognized that to merely increase the light intensity of the light sources used in the housing in order to obtain more light is not the answer. High intensity lamps create too much heat and in a confined space can materially interfere with the operation of the apparatus or even cause damage thereto. Thus, the filtration system of the present invention color-corrects the filament temperature of an incandescent light source without generating additional heat. Additionally, the range of color correction is of particular significance. If the illumination is much below 5000 degrees K, the light emitted will turn yellow, while above 5500 degrees K the emitted light appears to have a blue cast.

Maximum contrast is extremely important. It has been said that an increase in contrast of 1% can produce the same increase in the ability to see an object as an increase of 15% in illumination level. However, illumination level increases in some given circumstances are not readily available because of excessive heat generation, such as is the case if a halogen lamp were to be used, which excessive heat generation is avoided by the present invention.

Additional advantages of the present invention should also be referred to. The high efficiency and effectiveness of the filtered illumination system under the conditions utilized establishes a standards which is readily reproduced but can be varied. Being able to achieve such a standard is of great value when testing the contrast sensitivity characteristics of the eyes.

For example, by providing a plurality of test patterns that vary in their functional characteristics, particularly contrast, or by interposing filter means along the viewing path for reducing the contrast on the test pattern, night vision conditions can be simulated because they can be readily keyed to the maximum contrast standard of the invention which simulates daylight at noon. As vision conditions vary from dawn to dusk, such changes can also be simulated if desired. Because the invention provides a reproducible standard, a substantial improvement is provided in testing for point acuity, depth perception, color perception, lateral/vertical phoria, near point acuity, and lateral near points phoria inasmuch as these attributes can be tested under a variety of contrast conditions. This improvement can be useful in applications such as testing for night driving abilities, the extent that cataracts have developed, and color perception under varying contrast conditions.

While particular embodiments of the invention have been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

We claim:

1. In a vision testing apparatus wherein a light-occluding housing includes vision testing transparencies movable into a viewing position relative to a viewing area and light source means positioned relative to said transparencies to illuminate same for viewing, the improvement comprising;

blue filtering means interposed between said light source means and said viewing area, said light source means is an incandescent bulb with said blue filtering means positioned on the light transmitting surface thereof; and said blue filtering means include a coating having a coloration shade, a thickness and a density that, in cooperation with said light source means, provides ilumination of said transparencies in the range of approximately 5000 to 5500 degrees K and maintains substantially consistent illumination of said transparencies throughout variations in line voltage input to the vision testing apparatus of beween about 110 and about 135 volts, said substantially consistent illumination being white in color and avoiding off-color illumination experienced by blue filters other than said blue filtering means, including the development of orange and yellow tinged illumination of the transparencies at input line voltage variations beween said about 110 and about 135 volts.

2. The vision testing apparatus of claim 1, wherein said transparencies are mounted on a rotatable drum within which there are a pair of said light source means and said filtering means that establish a near point testing station and a far point testing station.

3. The vision testing apparatus of claim 2, wherein said light source means include tungsten filaments.

4. The vision testing apparatus of claim 1, wherein said light source means include tungsten filaments.

5. The vision testing apparatus of claim 2, wherein said filtering and light source means cooperatively provide illumination in the range of approximately 5000 to 5200 degrees K.

6. The vision testing apparatus of claim 1, wherein filter means are provided between said light source means and said viewing area, said filter means being for reducing contrast on the test pattern.

7. In a vision testing apparatus including: a base, a light-occluding casing carried by said base;

a drum member rotatably supported in said casing, means for rotating said drum member, said drum member having a periphery, said drum member having a vision test station disposed along said periphery of the drum member;

a test pattern carried by said drum member in position to be selectively moved into alignment with the vision test station, said test pattern having a plurality of characters;

viewing means carried by said casing including lens means adapted for optical alignment with said test pattern, the improvement comprising:

said vision test station including a tungsten filament light source, and blue colored filtering means is interposed beween said light source and an internal test pattern, said colored filtering means correcting the color of said light source to approximate the color temperature that is generally charcateristic of daylight lighting conditions said colored filtering means includes a coating having a coloration shade, a thickness and a density that, in cooperation with said light source, provides illumination of said internal test pattern at a color temperature value that is in the range of approximately 5000 to 5500 degrees K and imparts substantially consistent illumination of said internal test pattern throughout variations in line voltage input to the vision testing apparatus of between about 110 and about 135 volts, said substantially consistent illumination being white in color and avoiding off-color illumination experienced by blue filters other than said colored filtering means, including the development of orange and yellow tinged illumination of the internal test pattern at input line voltage variations between said about 110 and about 135 volts.

8. The vision testing apparatus of claim 7, wherein said light source is in the form of a bulb of clear glass with said coating on the surface thereof.

9. The vision testing apparatus of claim 7, wherein said color temperature value is within the general range of approximately 5000 to 5200 degrees K.

10. A method for testing vision in conjunction with a vision testing apparatus having a base, a light-occluding casing carried by said base, a test pattern positioned within said light-occluded casing, and a light source for providing translumination of said test pattern, said method including:

interposing a colored filtering means along a viewing path between the light source and the subject being tested;

simulating daylight lighting conditions within the light-occluded casing by selecting the filtering means such that said translumination of the test pattern corrects the color of said translumination to approximate the color temperature that is generally characteristic of daylight lighting conditions;

wherein said colored filtering means is blue and wherein said simulating step includes selecting the color temperature to be between about 5000 and 5500 degrees K; and maintaining said daylight lighting conditions substantially consistent throughout variations in line voltage input to the apparatus of between about 110 and about 135 volts in order to provide a reproducible illumination standard that is white in color, said maintaining step also avoiding off-color illumination experienced by blue filters other than said colored filtering means, including the development of orange and yellow tinged illumination of the test pattern at input line voltage variations between said about 110 and about 135 volts.

11. The vision testing method according to claim 10, wherein said interposing step is carried out at a location between the light source and the test pattern.

12. The vision testing method according to claim 10, wherein the vision testing that is carried out measures the contrast sensitivity characteristics of the eyes, and wherein said method includes varying the contrast of the test pattern in a controlled manner.

13. The vision testing method according to claim 12, wherein said varying is carried out by providing a plurality of test patterns that are characterized by differing contrast attributes thereof.

14. The vision testing method according to claim 12, wherein said varying is carried out by filter means for reducing the contrast of the test pattern.

15. The vision testing method according to claim 10, wherein said interposing step is carried out on a surface of the light source.

16. The vision testing method according to claim 10, wherein said interposing step is carried out at a location separate from the light source.

* * * * *